United States Patent
Hissong

(10) Patent No.: US 7,179,238 B2
(45) Date of Patent: Feb. 20, 2007

(54) APPARATUS AND METHODS FOR DIRECTLY DISPLACING THE PARTITION BETWEEN THE MIDDLE EAR AND INNER EAR AT AN INFRASONIC FREQUENCY

(75) Inventor: James B. Hissong, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 676 days.

(21) Appl. No.: 10/151,301

(22) Filed: May 21, 2002

(65) Prior Publication Data

US 2003/0220536 A1    Nov. 27, 2003

(51) Int. Cl.
    A61H 23/00    (2006.01)
(52) U.S. Cl. .......................................... 601/46; 607/57
(58) Field of Classification Search ................. 601/10, 601/41, 46, 76, 77; 607/55–57, 136–137; 600/25, 379, 552, 559; 623/10
    See application file for complete search history.

(56) References Cited

U.S. PATENT DOCUMENTS

| 4,757,807 | A | 7/1988 | Densert et al. |
| 5,421,818 | A | 6/1995 | Arenberg |
| 5,456,654 | A | 10/1995 | Ball |
| 5,474,529 | A | 12/1995 | Arenberg |
| 5,476,446 | A | 12/1995 | Arenberg |
| 5,554,096 | A | 9/1996 | Ball |
| 5,624,376 | A | 4/1997 | Ball et al. |
| 5,795,287 | A | 8/1998 | Ball et al. |
| 5,800,336 | A | 9/1998 | Ball et al. |
| 5,857,958 | A | 1/1999 | Ball et al. |
| 5,897,486 | A | 4/1999 | Ball et al. |
| 5,913,815 | A | 6/1999 | Ball et al. |
| 6,159,171 | A | 12/2000 | Densert et al. |
| 6,251,062 | B1 | 6/2001 | Leysieffer |
| 6,592,512 | B2 * | 7/2003 | Stockert et al. ............... 600/25 |
| 6,629,938 | B1 | 10/2003 | Engvall et al. |

FOREIGN PATENT DOCUMENTS

| EP | 0 266 474 B1 | 5/1988 |
| WO | WO 83/02556 | 8/1983 |

(Continued)

OTHER PUBLICATIONS

"Transmission of Square Wave Pressure Pulses through the Perilymphatic Fluid in Cats", Acta Otolaryngol (Stockh) 1986; 102: 186-193, Densert, Erlandsson, H. Sheppard.

(Continued)

*Primary Examiner*—Quang D. Thanh

(57) ABSTRACT

An apparatus for displacing a partition between a middle ear and an inner ear to treat the symptoms of Meniere's disease or endolymphatic hydrops comprises a treatment member for being disposed in the middle ear adjacent the partition and a driver for driving the treatment member to move against the partition to thereby displace the partition at an infrasonic frequency to influence fluid distribution in the inner ear. A method for treating an ear comprises the steps of disposing a treatment device within the middle ear and moving at least a portion of the treatment device against the partition at an infrasonic frequency to displace the partition to influence fluid in the inner ear.

37 Claims, 7 Drawing Sheets

FOREIGN PATENT DOCUMENTS

| WO | WO 93/08775 | 5/1993 |
| WO | WO 97/23178 | 7/1997 |
| WO | WO 00/01331 | 1/2000 |
| WO | WO 00/01346 | 1/2000 |
| WO | WO 00/10484 | 3/2000 |

OTHER PUBLICATIONS

"Transmission of Low Frequency Pressure Steps to the Perilymphatic Fluid", Acta Otalaryngol 91: 55-64, 1981, Ove Densert, Bjorn Carlborg and John Stagg.

"Immediate Effects of Middle Ear Pressure Changes on the Electrocochleographic Recordings in Parties with Meniere's Disease: A Clinical Placebo-Controlled Study", The American Journal of Otology 18:726-733, 1997.

Barbara Densert, Ove Densert Stig Arlinger, Kornel Sass, Lars Odkvist.

"Overpressure in Treatment of Meniere's Disease", B. Densert, O. Densert, Halmstad, Sweden, LARYNGOSCOPE, vol. 92, No. 11, Nov. 1982.

"Transmission of Complex Pressure Waves through the Perilymphatic Fluid in Cats", Acta Otolaryngol (Stockh) 1986; 102:403-409, B. Densert, O. Densert, B. Erlandsson and H. Sheppard.

"Functional Patency of the Cochlear Aqueduct", Annals of Otology, Rhinology and Laryngology, Mar.-Apr. 1982, vol. 91, No. 2, B. Densert, B. Carlborg, O. Densert.

"Effects of Middle Ear Changes on Clinical Symptoms in Patients with Meniere's Disease—a Clinical Multicentre Placebo-controlled Study", L.M. Odkvist, S. Arlinger, E. Billermark.

B. Densert, S. Lindholm and J. Wallqvist, Acta Otalaryngol 2000; Suppl 543: 99-101.

Control of Symptoms in Patients with Meniere's Disease Using Middle Ear Pressure Applications.

Two Years Follow-up, B. Densert and K. Sass, Acta Otolaryngol 2001; 121: 616-621.

Product Catalog, Medtronic Xomed, Inc., The Meniett™ Low-Pressure Pulse Generator, Feb. 2003.

A Review of Medical Treatment for Meniere's Disease, J. Claes and P.H. Van De Heyning, Acta Otolaryngol 2000, Suppl 544: 34-39.

"Middle Ear Overpressure Treatment of Endolymphatic Hydrops in Guinea Pigs", Yasuhiko Sakikawa and Robert S. Kimura, ORL 1997; 59: 84-90.

Salt, A. et al "*Longitudinal Endolymph Movements and Endocochlear Potential Changes induced by Stimulation at Infrasonic Frequencies*" Acoustical Society of America, pp.847-856 (1999).

\* cited by examiner

APPARATUS AND METHODS FOR DIRECTLY DISPLACING THE PARTITION BETWEEN THE MIDDLE EAR AND INNER EAR AT AN INFRASONIC FREQUENCY

BACKGROUND OF THE INVENTION

1. Field of the Invention

The invention relates to apparatus and methods for influencing the fluid system of the inner ear for treating the symptoms of Meniere's disease or endolymphatic hydrops and, more particularly, to such apparatus and methods for treating symptoms of diseases and conditions of the ear, such as Meniere's disease or endolymphatic hydrops.

2. Description of the Related Art

Meniere's disease is a chronic disease from which millions of people suffer. The origin of Meniere's disease is believed to be an imbalance in the hydrodynamic system of the inner ear, described as endolymphatic hydrops. In addition to the severity of the symptoms of Meniere's disease, which include fluctuating hearing loss, fluctuating tinnitus, fluctuating sense of fullness in the ear and fluctuating vertigo, the unpredictable onset of the symptoms creates a major handicap for sufferers of Meniere's disease.

As illustrated in FIG. 1, the human ear 10 includes three primary spaces, the outer ear canal 12, also known as the external acoustic meatus, the middle ear 14, and the inner ear 16. The middle ear, also known as the tympanic cavity, is adjacent the outer ear canal and is separated from the outer ear canal by the tympanic membrane 18, also known as the ear drum. The inner ear includes the cochlea 20 formed of the scala vestibuli 22 and the scala tympani 24 which surround the cochlear duct 26 (cross-hatched to simplify visualization). The cochlear duct is filled with endolymphatic fluid supplied by the endolymphatic sac 28. The scala vestibuli 22 and scala tympani 24 are filled with perilymph fluid that moves in response to displacement of the footplate or base 29 of the stapes 30 in the oval window 32. The stapes is one of a series of small bones (ossicles) in the middle ear connecting the tympanic membrane 18 with the inner ear. The inner ear is separated from the middle ear by an anatomical partition formed of the stapes footplate 29 at the oval window 32 and the round window membrane 34. Since the stapes footplate is part of the stapes, the entire stapes may be considered as forming part of the partition. Movement of the stapes footplate in the oval window 32 causes the perilymph fluid to move within the scala vestibuli affecting the endolymphatic fluid within the cochlear duct to effect hearing. The round window membrane 34 separates the scala tympani 24 of the inner ear from the middle ear 14 and operates to dissipate waves formed in the perilymph fluid.

The symptoms of Meniere's disease are believed to be caused by endolymphatic hydrops, an excessive buildup of endolymphatic fluid in the cochlea. Meniere's disease is typically characterized by varying degrees of four classic symptoms: 1) fluctuating hearing loss, the extent of which increases over time; 2) fluctuating tinnitus, causing various sounds, described as whining, roaring or other sounds; 3) fluctuating sense of fullness, or a "plugged ear" sensation similar to a sensation one experiences upon descending from a mountain and being unable to clear or equalize the pressure in one's ear; and 4) fluctuating vertigo, or dizziness that can range from mild to severe. As used herein, the terms "symptoms of Meniere's disease" means some or all of the above symptoms in that the method and apparatus of the present invention can provide treatment for any of the above symptoms, individually or together, which are caused by endolymphatic hydrops.

An early method of treating a person with Meniere's disease was developed empirically and includes placing the patient in a pressure chamber to alleviate the symptoms. The theory of the treatment is to place pressure on the inner ear fluids to attempt to reduce the amount of fluid in the endolymph system, specifically the endolymph fluid within the scala media (not shown) of the cochlear duct 26.

Another method includes applying air pressure pulses to the middle ear by way of a hole through the tympanic membrane. The hole allows the pressure pulses to pass from the outer ear canal into the middle ear. It is believed that the round window membrane moves in response to the pressure changes and transfers the movement/pressure changes to the perilymph fluid, which resultantly transfers the motion/pressure to the endolymph fluid through membranes separating those two distinct fluids. The oval window may also act to transfer varying pressure to the perilymph fluid; and, accordingly, hereinafter references to displacement of the round window membrane also are meant to include displacement of the stapes footplate at the oval window. U.S. Pat. No. 4,757,807, WO Publications No. 83/02556, No. 93/08775, No. 97/23178, No. 00/01331, No. 00/01346 and No. 00/10484, European Patent No. 266474 B1, Acta Otolaryngol 102:186–193, 1986, Acta Otolaryngol 91:55–64, 1981, Acta Otolaryngol 102:403–409, 1986, Laryngoscope V.92, No. 11, 1982; 1285–92, Carlborg et al 1982 V. 91, No. 2, American Journal of Otology 18:726–733, Acta Otolaryngol 2000 543:99–101 and Acta Otolaryngol 2001 121:616–621 are representative of the above method which is also exemplified by the Meniett portable pressure pulse generator sold by Medtronic Xomed, Inc., Jacksonville, Fla.

In order to practice the above method, a hole formed in the tympanic membrane 18 is fitted with a ventilation tube 36, as shown in FIG. 1. After the ventilation tube 36 is inserted into the tympanic membrane, pressure pulses are generated and transmitted into the outer ear canal 12 by way of a tube having an ear plug sealing the tube against the walls of the outer ear canal so that the pressure pulses vary the pressure in the middle ear through the vent formed by the ventilation tube to influence the fluid system of the inner ear through the round window membrane. That is, the ventilation tube 36 allows air to pass from the outer ear canal 12 to the middle ear 14, thereby allowing the pressure pulses applied to the outer ear canal to cause the pressure in the middle ear to fluctuate. Although the actual mechanisms are still not fully understood, one theory of action that reduces endolymphatic hydrops is that the action of the pressure pulses on the fluid system combine with other physiologic reactions in the ear to force excess endolymph fluid into the endolymphatic sac 28.

The above method of treating Meniere's disease relies on applying a series of pressure pulses biased by a positive pressure $P_s$, as illustrated in FIG. 2. The pressure pulses are applied to the outer ear canal to transmit varying pressure changes through the ventilation tube 36 into the middle ear in order to displace the round window membrane 34. The series of pressure pulses developed as a result of empirical observations have been used to treat patients suffering from Meniere's disease.

The pressure pulses applied in the past have included sine waves, static and alternating components, a predetermined overpressure superimposed on pressure oscillations, square waves and low frequency sine waves superimposed on square wave pressure pulses. The Densert et al U.S. Pat. No.

6,159,171 shows pressure pulses generated by the Meniett portable pressure pulse generator in FIG. 3 thereof and provides a description thereof in columns 3 and 4.

SUMMARY OF THE INVENTION

The present invention is generally characterized in an apparatus for displacing a partition between a middle ear and an inner ear to treat the symptoms of Meniere's disease. The apparatus comprises a treatment member for being disposed in the middle ear adjacent the partition and a driver for driving the treatment member to move aginst the partition to thereby displace the partition at an infrasonic frequency to influence fluid distribution in the inner ear. The treatment member may comprise a transducer, a floating mass treatment member or a free-floating magnet treatment member. The transducer may comprise a piezoelectric transducer, an electromagnetic transducer, an electromechanical transducer or any other type of transducer that mechanically vibrates, reciprocates, oscillates or moves in response to a drive signal transmitted thereto. The driver generates the drive signal used to drive the treatment member, and the drive signal may be mechanical, electrical, magnetic, pneumatic, acoustic or the like. The apparatus may include a housing for the treatment member and/or for one or more connectors coupling the treatment member to the driver.

A method for treating an ear in accordance with the present invention is generally characterized in the steps of disposing a treatment device within the middle ear adjacent the partition between the middle ear and the inner ear and moving at least a portion of the treatment device against the partition at an infrasonic frequency to displace the partition to influence fluid displacement in the inner ear. At least a portion of the treatment device may be moved against the round window membrane such that the round window membrane is displaced by the treatment device. At least a portion of the treatment device may be moved against the stapes such that the stapes footplate is displaced by the treatment device. A treatment member of the treatment device may be moved against the partition at an infrasonic frequency to displace the partition at the infrasonic frequency. Movement of at least a portion of the treatment device to displace the partition may be used to alleviate the symptoms of Meniere's disease and may be used to alleviate vertigo, tinnitus, fullness of the ear and/or hearing loss.

The present invention will become better apparent from the following description of the preferred embodiments taken in conjunction with the accompanying drawings, wherein like parts in each of the several figures are identified by the same reference numeral.

DESCRIPTION OF THE PREFERRED EMBODIMENTS

Figure 1:
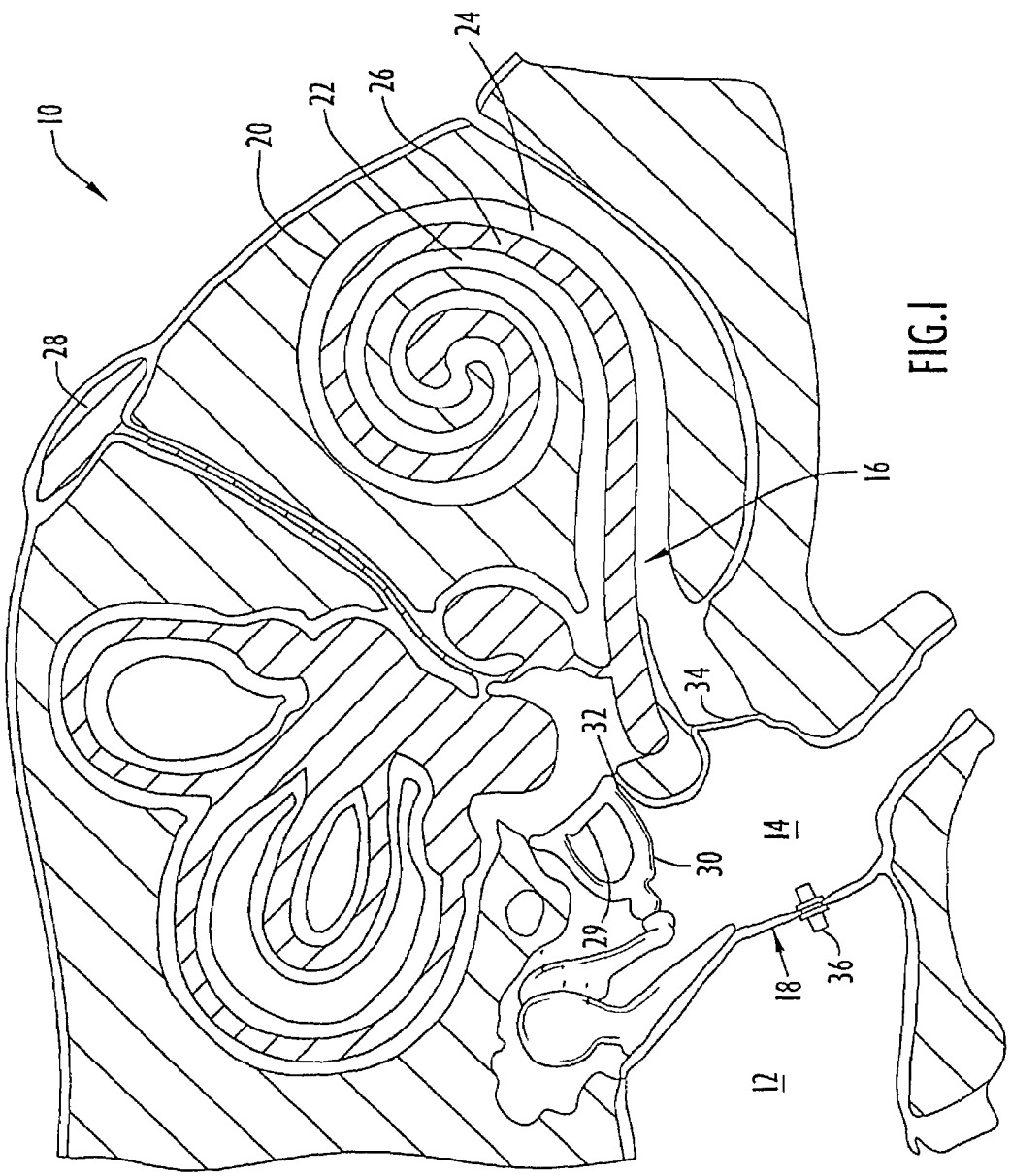
FIG. 1 is a broken section of a human ear, showing a portion of the outer ear canal, middle ear and inner ear.
Figure 2:
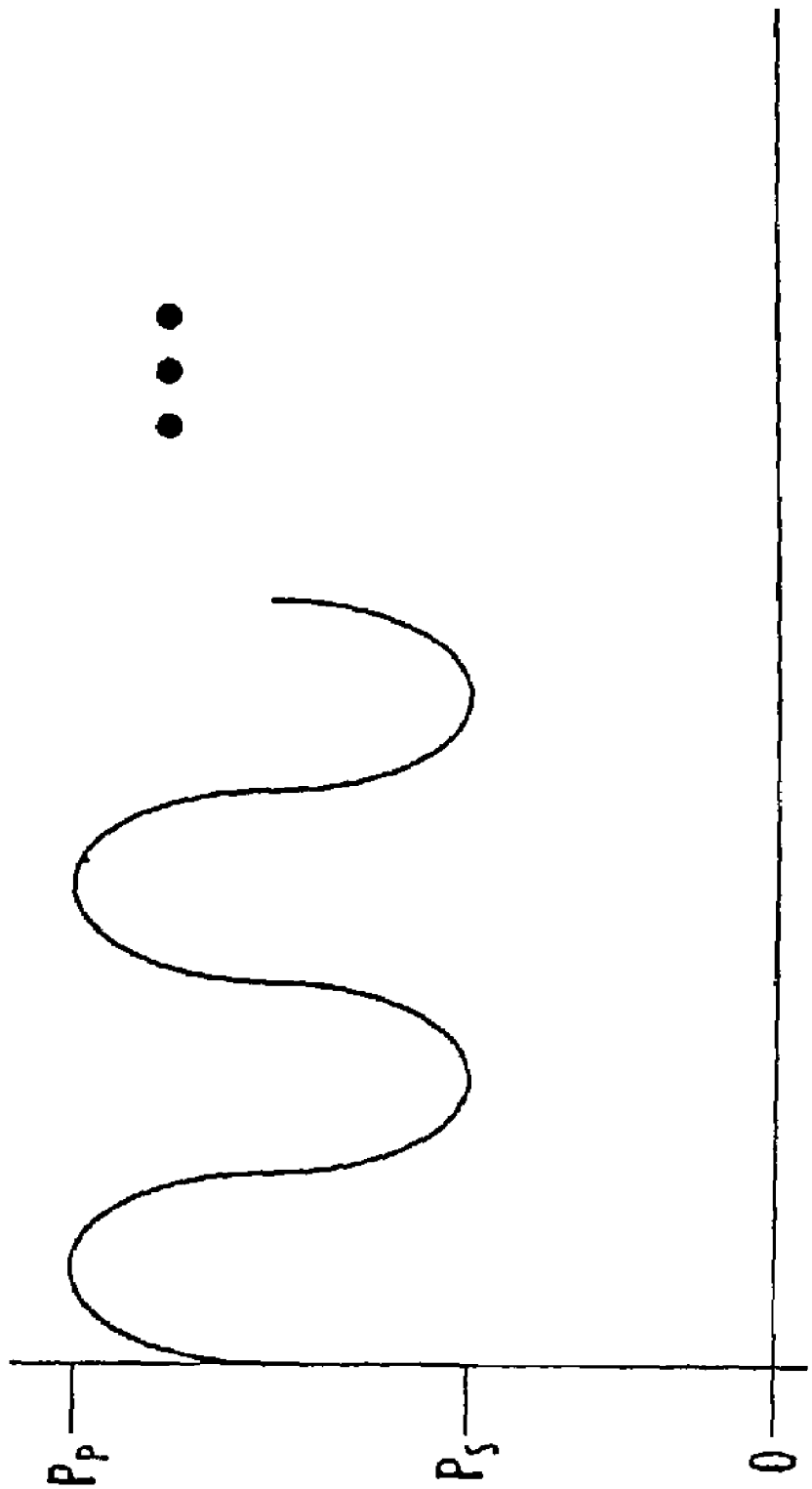
FIG. 2 is a graph of a pressure wave in the form of a sine wave biased by a positive pressure in accordance with the prior art.

Prior methods of treating Meniere's disease involve altering the air pressure within the middle ear 14 of the ear, illustrated in FIG. 1, to thereby indirectly influence fluid distribution in the inner ear 16. Prior methods of treating Meniere's disease have not involved moving at least a portion of a treatment device or apparatus against the partition between the middle ear and the inner ear to move or displace the partition at an infrasonic frequency. In accordance with the present invention, a treatment device or apparatus is placed adjacent or in contact with the partition, and the treatment device is powered or driven so that at least a portion of the treatment device mechanically vibrates, reciprocates, oscillates or otherwise moves against the partition. The partition is moved or displaced by the treatment device at an infrasonic frequency to influence fluid distribution in the inner ear to treat diseases and other conditions of the ear such as Meniere's disease. As used herein, "infrasonic frequency" is used synonymously with "subsonic frequency" and refers to a sub-audible frequency of movement or displacement of the partition that is less than, below or lower than the frequency of movement or displacement experienced by the stapes footplate 29 in normal sound generation and in hearing restoration systems.

Figure 3:
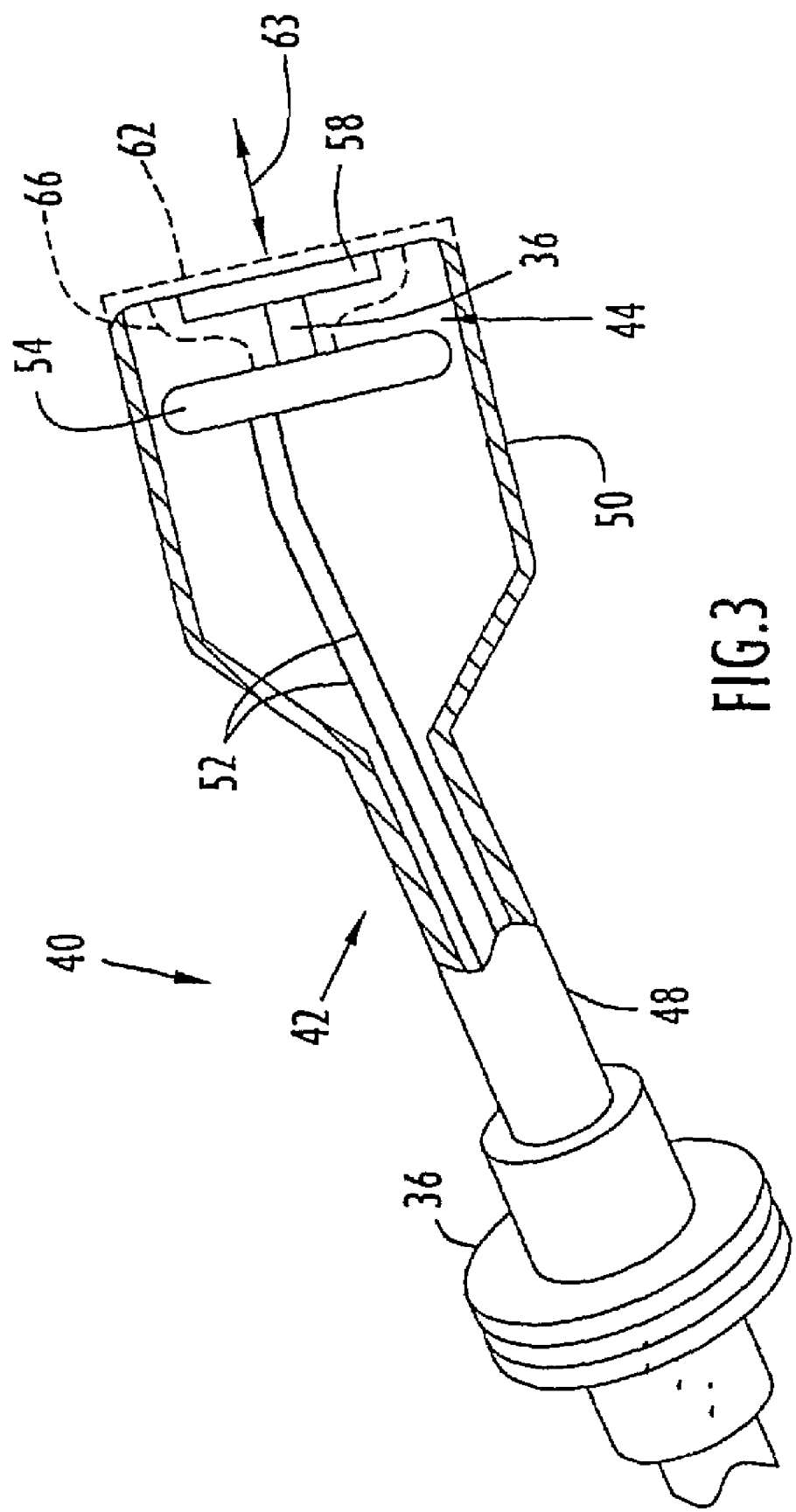
FIG. 3 is a broken perspective view, partly in section, of a treatment device according to the present invention for displacing the partition between the middle ear and the inner ear at an infrasonic frequency.
Figure 4:
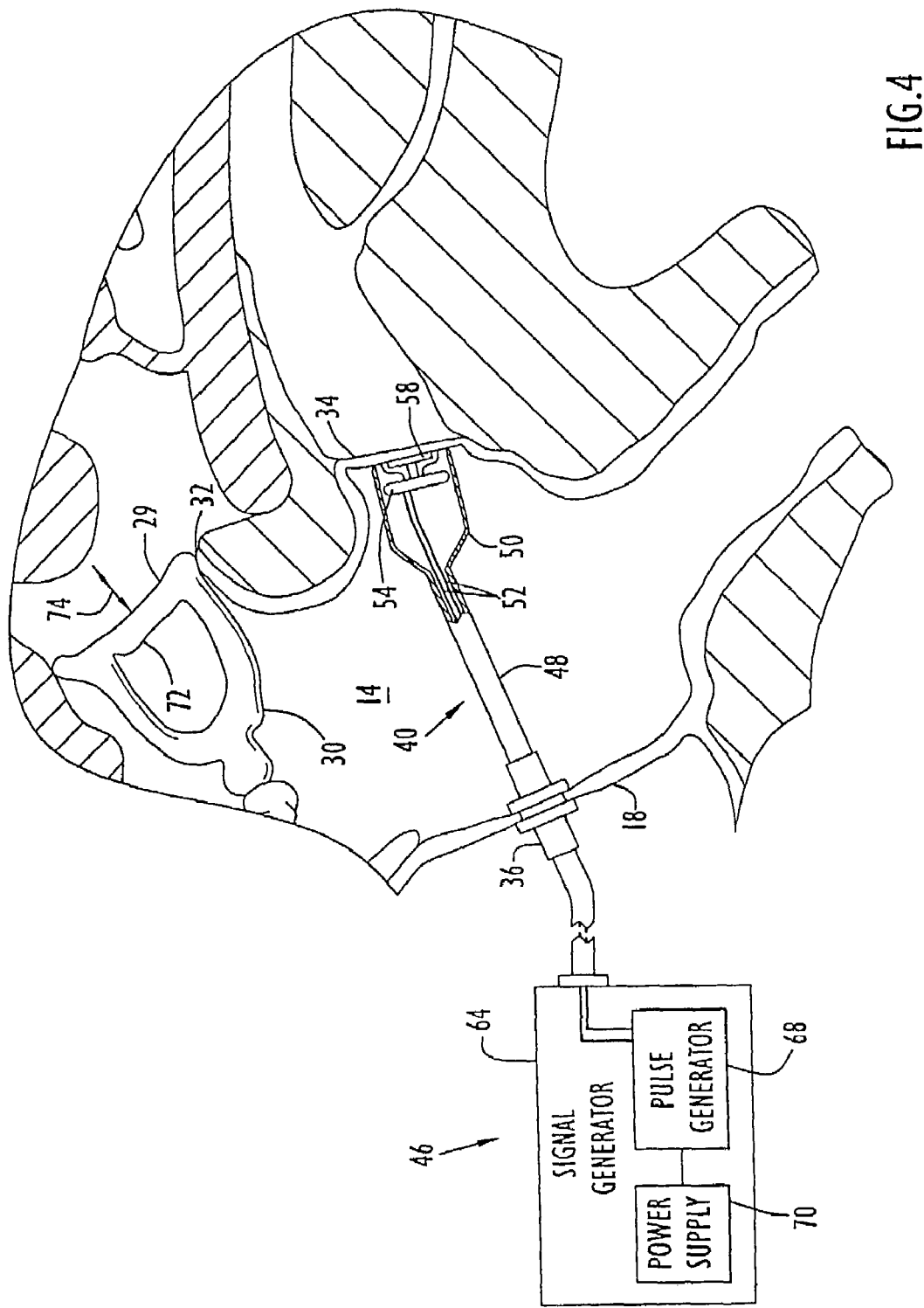
FIG. 4 depicts a method for treating a human ear in accordance with the present invention in which a movable treatment member of the treatment device of FIG. 3 contacts the round window membrane of the partition between the middle ear and the inner ear.

A treatment device or apparatus 40 according to the present invention is illustrated in FIGS. 3 and 4 and includes a housing 42, a treatment member 44 disposed in housing 42 and a driver 46 for driving or powering the treatment member 44 to vibrate, reciprocate, oscillate or otherwise move to effect displacement of the partition between the middle ear 14 and inner ear 16 at an infrasonic frequency as explained further below. The housing 42 comprises an elongate sleeve 48 connected with an enlarged hood 50 at a forward end of sleeve 48. The hood 50 has an open forward end communicating with an interior, and the treatment member 44 is disposed in the interior of hood 50 adjacent its open forward end. One or more connectors 52 extend proximally or rearwardly from the treatment member 44, the one or more connectors 52 extending through the sleeve 48 to the driver 46 as shown in FIG. 4. The one or more connectors 52 transmit one or more drive signals from the driver 46 to the treatment member 44 to drive or power the treatment member to vibrate, reciprocate, oscillate or otherwise move to effect displacement of the partition at an infrasonic frequency. In the case of treatment device 40, the treatment member 44 includes a transducer 54, a shaft 56 extending distally or forwardly from the transducer 54 and a plunger 58 at a forward end of shaft 56, the plunger 58 forming a distal end of the treatment device 40. The plunger 58 is flat or planar but may have any desired configuration suitable for contacting a selected portion of the partition between the middle ear 14 and the inner ear 16 and, in particular, the round window membrane 34.

The housing 42 may be flexible or resilient to facilitate introduction of the distal end of the treatment device in the middle ear 14 through a conventional ventilation tube 36 disposed in an opening or vent in the tympanic membrane 18 and to facilitate positioning of the treatment member 44 adjacent a selected portion of the partition between the middle ear 14 and the inner ear 16. Where the cross-sectional dimension of the treatment device to be inserted in the middle ear 14 is larger than the lumen of the ventilation tube, the treatment device may be designed to resiliently deflect or collapse to permit insertion through the ventilation tube. Alternatively, the treatment device can be designed with a fixed cross-sectional dimension sized to fit through the ventilation tube. Of course, the treatment device can be introduced in the vent or opening without a ventilation tube, and the vent or opening can be formed with a size large enough to accommodate the treatment device therethrough. The housing 42 can be provided with or without a hood and, depending on the design of the treatment member and the one or more connectors, the treatment device can be provided without a housing. It is preferred that the housing be constructed from a biocompatible material. The open forward end of the hood 50 may be closed by a resilient, distensible or stretchable membrane 62, shown in dotted lines in FIG. 3. The membrane 62 resiliently stretches or distends when the treatment member 44 is moved as explained further below and as shown by arrow 63 in FIG. 3. Preferably, the membrane 62 is made of biocompatible material.

The transducer 54 may be a piezoelectric transducer, an electromagnetic transducer, an electromechanical transducer, a pneumatic transducer or any othertype of transducer having at least a portion that mechanically vibrates, reciprocates, oscillates or otherwise moves in response to a driving or power signal transmitted thereto. The transducer 54 may be powered or driven by an electrical drive signal generated by driver 46; and, therefore, the one or more connectors 52 may comprise one or more electrical signal wires that couple the transducer 54 to a signal generator 64 of driver 46. The plunger 58 is mounted perpendicular to the shaft 56 but can be mounted at any suitable angle to enhance contact of the plunger with a selected portion of the partition between the middle ear 14 and the inner ear 16. The shaft 56 and plunger 58 can be enclosed in a shield or cover 66 formed by a resilient membrane made of biocompatible material as shown in dotted lines in FIG. 3. Of course, the treatment member 44 can be provided without a shield 66 and the shaft 56 and/or plunger 58 may be made of biocompatible material.

The driver 46 may be disposed proximally of the tympanic membrane 18 when the distal end of the treatment device is inserted in the middle ear and may comprise a pulse generator 68, a power supply 70 for powering the pulse generator 68 and/or a suitable processor. The pulse generator and processor may be designed as a single unit or as separate units. Of course, the power supply 70 could be separate and independent of the driver 46. The driver 46 may be located outside of the ear or may be implanted within the ear, either permanently or temporarily. The driver 46 may be removably coupled with the remainder of the treatment device, thereby allowing all or a portion of the remainder of the treatment device to be implanted in the ear, either temporarily or permanently, while the driver 46 remains external to and not implanted in the ear.

In operation of the treatment device 40, an electric charge or current generated by driver 46 is supplied as a drive signal through the one or more connectors 52 to the transducer 54. The pulse generator 68 assists in producing a drive signal in a form suitable for the type of transducer used in the treatment member. Application of the charge or current to the transducer 54 causes the transducer to vibrate, oscillate or reciprocate according to the characteristics of the drive signal supplied by driver 46. Movement of transducer 54 causes corresponding displacement of shaft 56 which in turn displaces the plunger 58 correspondingly. Accordingly, the plunger 58 vibrates, oscillates or reciprocates relative to the hood 50 as represented by arrow 63 in FIG. 3. Where the membrane 62 is provided on hood 50, the membrane 62 will resiliently stretch and contract as the plunger 58 is moved. The drive signal generated by driver 46 causes the treatment member 44 to vibrate, oscillate or reciprocate at an infrasonic or subsonic frequency. By varying the characteristics of the drive signal, the infrasonic or subsonic frequency can be varied to obtain various uniform or constant infrasonic or subsonic frequencies or various non-uniform or variable frequencies. Accordingly, for a given treatment procedure, the frequency of movement or displacement of the treatment member 44 and, therefore, for the partition, may be maintained at a selected uniform or constant infrasonic frequency or may be varied to incorporate a plurality of selected infrasonic frequencies. The displacement distance for the treatment member and, therefore, for the partition, may also be varied by varying the characteristics of the drive signal such that the displacement distance may remain constant throughout a given treatment procedure or may be varied throughout a given treatment procedure.

In a method for treating a human ear to alleviate the symptoms of Meniere's disease in accordance with the present invention, the distal end of the treatment device 40 is introduced through the vent or opening in tympanic membrane 18, such as by being introduced through the ventilation tube 36, to position the treatment member 44 in the middle ear 14 while the driver 46 remains on the opposite side of the tympanic membrane 18 as shown in FIG. 4. The plunger 58 is positioned adjacent or in contact with a selected portion of the partition between the middle ear 14 and the inner ear 16. In one method according to the present invention, the selected portion of the partition is the round window membrane 34, and the plunger 58 is positioned adjacent or in contact with the round window membrane 34 as shown in FIG. 4. In another method according to the present invention, the selected portion of the partition is the stapes footplate 29, and the plunger 58 is positioned adjacent or in contact with the stapes at an appropriate location to cause the stapes footplate 29 to be moved or displaced in the direction of arrow 74 in FIG. 4. As an example, the plunger 58 may be placed adjacent or in contact with the stapes footplate 29 at location 72, as permitted by the flexibility of housing 42 and, in particular, bending of sleeve 48. Of course, the treatment device may be provided with any suitable attachment structure for releasably attaching the treatment member or another portion of the treatment device to the partition or other anatomical structure in the ear for greater stability and enhanced securement. When the plunger 58 is positioned in contact with the round window membrane 34 as shown in FIG. 4, a forward edge of hood 50 is in contact with the round window membrane for added stability.

Once the plunger 58 has been properly positioned adjacent or in contact with a selected portion of the partition, the driver 46 is powered or activated via the power supply to deliver an appropriate electrical or other form of drive signal to the transducer 54, thusly causing the transducer to vibrate, oscillate or reciprocate. The plunger 58 is correspondingly moved against the selected portion of the partition such that the selected portion of the partition, i.e., the round window membrane 34, is correspondingly displaced to influence fluid distribution in the inner ear 16. Accordingly, mechanical motion of at least a portion of the treatment device is used to stimulate motion of inner ear fluids via direct application of the mechanical motion against the partition. By affecting fluid distribution in the inner ear in this manner, the symptoms of Meniere's disease are alleviated or treated including alleviation or treatment of tinnitus, vertigo, hearing loss and/or fullness of the ear.

Figure 5:
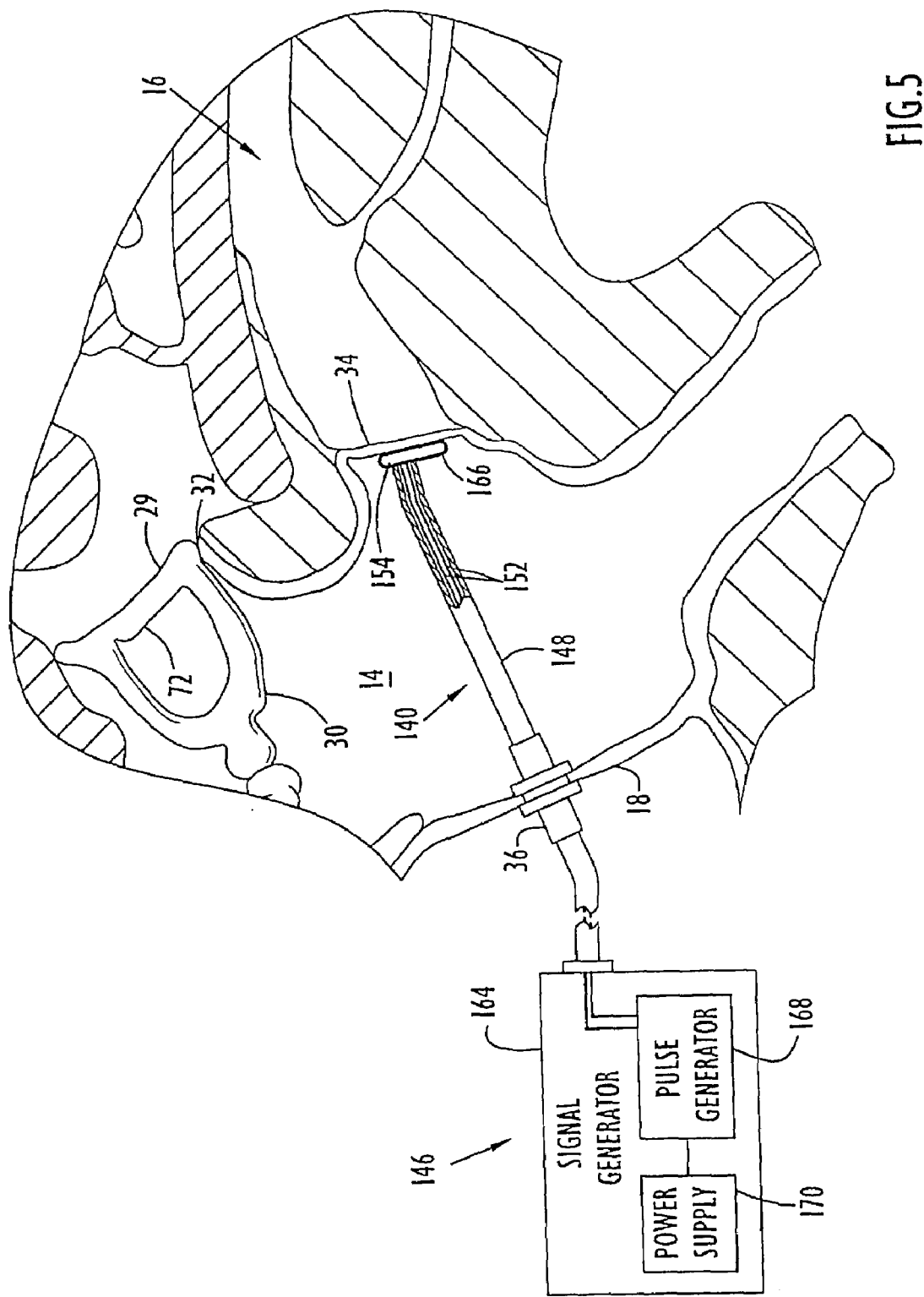
FIG. 5 depicts an alternative method for treating a human ear in accordance with the present invention in which a movable treatment member of an alternative treatment device according to the present invention contacts the round window membrane.

An alternative method for treating a human ear to alleviate the symptoms of Meniere's disease in accordance with the present invention is illustrated in FIG. 5. The method shown in FIG. 5 is similar to the method of FIG. 4 but utilizes an alternative treatment device 140. Treatment device 140 is similar to treatment device 40 except that the treatment member for treatment device 140 includes transducer 154 without a shaft and plunger. Transducer 154 is covered by a shield 166 formed as a resilient membrane made of biocompatible material. In the method shown in FIG. 5, the transducer 154 is positioned adjacent or in contact with the selected portion of the partition, which is shown as constituting the round window membrane 34, and the transducer 154 itself is caused to move against the round window membrane 34 to correspondingly displace the round window membrane to influence the fluid distribution within the inner ear 16 as described above.

Figure 6:
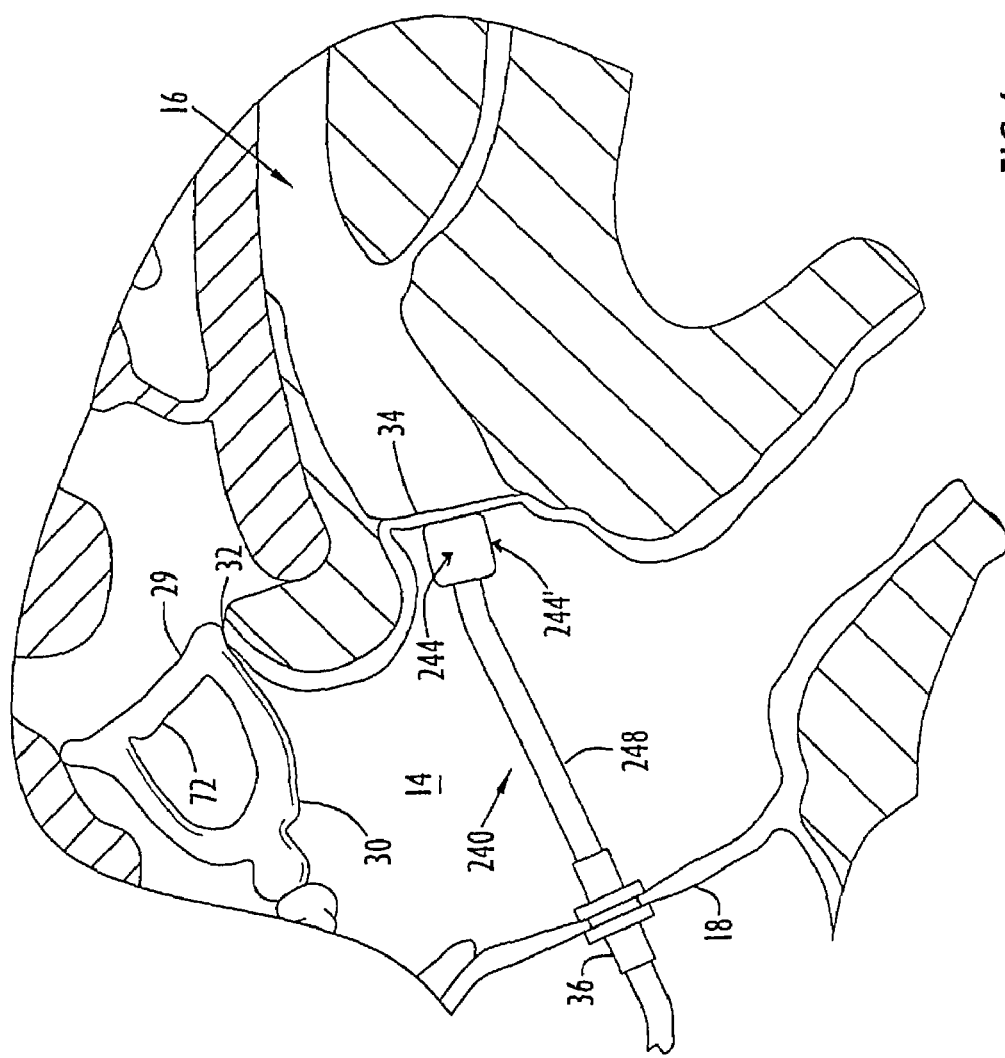
FIG. 6 depicts an alternative method for treating a human ear in accordance with the present invention utilizing alternative treatment members.

FIG. 6 is representative of further alternative methods for treating a human ear to alleviate the symptoms of Meniere's disease utilizing further alternative treatment members. FIG. 6 illustrates a treatment device 240 that is similar to treatment device 40 except that the treatment member 244 for treatment device 240 is a floating mass treatment member. The treatment member 244 comprises a floating mass within a coil, with the floating mass being stimulated by changing currents in the coil to cause oscillation or movement of the treatment member. In the method of FIG. 6, which is similar to the methods previously described, mechanical oscillation or movement of the floating mass treatment member 244 at an infrasonic frequency is applied against a selected portion of the partition, i.e., the round window membrane 34, for example, to correspondingly displace the selected portion at an infrasonic frequency. The floating mass treatment member 244 may be designed in accordance with the floating mass technology (FMT) used in the hearing aids of Symphonix Devices, Inc. and as represented by U.S. Pat. Nos. 5,456,654, 5,554,096, 5,624,376, 5,795,287, 5,800,336, 5,857,958, 5,897,486 and 5,913,815, the disclosures of which are incorporated herein by reference. Although the floating mass treatment member 244 is shown mounted to a sleeve 248 extending through a vent or opening in tympanic membrane 18, it should be appreciated that the floating mass treatment member 244 can be incorporated in a treatment device that is temporarily or permanently implanted in the ear.

The treatment member for the treatment device 240 may alternatively be designed as a free-floating magnet treatment member 244' including a hermetically sealed magnet free-floating in a cylinder attached to a plunger or the like and placed adjacent or in contact with the selected portion of the partition such as the round window membrane 34 in the method of FIG. 6. The magnet is stimulated by an electric current through a coil, causing the magnet to move against the partition such that the selected portion of the partition is moved at an infrasonic frequency. The free-floating magnet treatment member 244' may be designed in accordance with the hermetically sealed, free-floating magnet structure employed by Soundtec, Inc. in implantable aids for hearing and as represented by U.S. Pat. No. 4,606,329, the disclosure of which is incorporated herein by reference.

Figure 7:
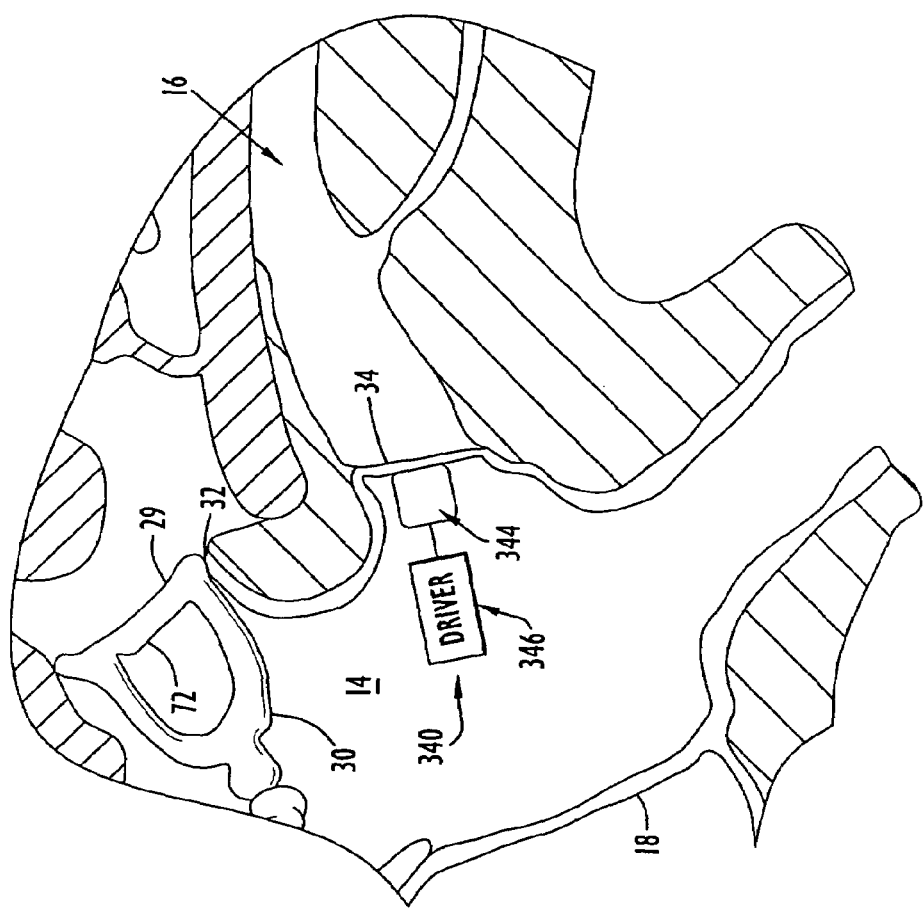
FIG. 7 depicts a further alternative method for treating a human ear in accordance with the present invention utilizing a further alternative treatment device according to the present invention.

Another alternative method of treating a human ear to alleviate the symptoms of Meniere's disease is illustrated in FIG. 7 and employs another alternative treatment device 340. The method depicted in FIG. 7 is similar to the methods described above except that the entire treatment device 340 is implanted in the middle ear 14. Accordingly, treatment member 344 and driver 346 of treatment device 340 are both implanted entirely in the middle ear 14 without any structure or components extending through the tympanic membrane 18. Driver 346 will be designed in accordance with the particular treatment member 344, which can be any suitable treatment member capable of moving against a selected portion of the partition, such as round window membrane 34.

Any treatment member capable of causing direct displacement of a selected portion of the partition to stimulate motion of inner ear fluids in response to a drive signal can be used in the treatment devices. The drive signal used to actuate the treatment member may include, but is not limited to, mechanical, electrical, magnetic, radio waves, pneumatic (air/fluid), and acoustic drive signals. The drive signal generated by the driver is appropriate for the particular treatment member to cause the treatment member to move in a manner to displace the selected portion of the partition. The driver produces a drive signal in a form suitable for the type of treatment member being used. For example, the driver can generate a series of pulses having predetermined characteristics that cause the treatment member to move back and forth in accordance with the series of pulses. The predetermined characteristics of the series of pulses can be, for example, pulses forming a sine wave of a particular infrasonic frequency and having a predetermined amplitude. The pulses may be delivered in waveforms as disclosed in related U.S. Patent Application entitled Apparatus and Methods for Treating Symptoms of Disease and Conditions of the Ear, filed concurrently herewith, the disclosure of which is incorporated herein by reference. The treatment member could be driven electromagnetically or in other manners capable of eliminating the need for connector wires. The power supply can be integral with or separate from the treatment device. A representative integral power supply may include a battery. A representative power supply that is separate from the treatment device may include an external DC source or an AC line connection. All or part of the treatment device can be implanted either partially or fully and may reside either temporarily or permanently within the ear. The treatment devices can be stabilized against a medial wall of the ear that contains the round window membrane when the treatment member is moved against the round window membrane. The housing, particularly the sleeve thereof, may serve as a handle to facilitate introduction and positioning of the treatment device in the middle ear. The treatment device can be self-controlled by the patient or may be controlled by an operator. The treatment device can be programmed to operate intermittently or cyclically to alleviate the symptoms of Meniere's disease or endolymphatic hydrops.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An apparatus for displacing a partition between a middle ear and an inner ear to treat the symptoms of Meniere's disease comprising
   a treatment member for positioning adjacent a selected portion of the partition; and
   a driver for driving said treatment member to move against the selected portion of the partition at an infrasonic frequency to influence fluid in the inner ear.

2. The apparatus recited in claim 1 wherein said treatment member comprises a transducer.

3. The apparatus recited in claim 2 wherein said treatment member includes a shaft connected to said transducer and a plunger connected to said shaft for moving against the selected portion of the partition.

4. The apparatus recited in claim 2 wherein said transducer comprises a piezoelectric transducer.

5. The apparatus recited in claim 4 wherein said driver generates an electrical signal to drive said transducer.

6. The apparatus recited in claim 1 wherein said treatment member comprises a floating mass treatment member.

7. The apparatus recited in claim 1 wherein said treatment member comprises a free-floating magnet treatment member.

8. The apparatus recited in claim 1 wherein said driver drives said treatment member to reciprocate.

9. The apparatus recited in claim 1 wherein said driver drives said treatment member to vibrate.

10. The apparatus recited in claim 1 wherein said driver drives said treatment member to oscillate.

11. An apparatus for displacing a partition between a middle ear and an inner ear to treat the symptoms of Meniere's disease comprising
    treatment means for positioning adjacent a selected portion of the partition; and
    driving means for driving said treatment means to move against the selected portion of the partition whereby the selected portion of the partition is displaced at an infrasonic frequency to influence fluid in the inner ear.

12. The apparatus recited in claim 11 wherein said treatment means comprises a transducer.

13. The apparatus recited in claim 12 wherein said transducer comprises a piezoelectric transducer.

14. The apparatus recited in claim 13 wherein said driving means comprises a signal generator for supplying an electrical signal to said transducer.

15. The apparatus recited in claim 14 wherein said driving means further comprises a pulse generator.

16. The apparatus recited in claim 11 wherein said treatment means comprises a floating mass treatment member.

17. The apparatus recited in claim 11 wherein said treatment means comprises a free-floating magnet treatment member.

18. The apparatus recited in claim 11 and further including a power supply for said driving means.

19. The apparatus recited in claim 18 wherein said power supply is integral with said apparatus.

20. A method for treating an ear, having a middle ear and an inner ear separated by a partition, to treat the symptoms of Meniere's disease comprising the steps of
    disposing a treatment member within the middle ear; and
    moving the treatment member against a selected portion of the partition to displace the selected portion of the partition at an infrasonic frequency to influence fluid in the inner ear.

21. The method for treating an ear recited in claim 20 wherein said step of moving comprises moving the treatment member against the round window membrane to displace the round window membrane.

22. The method for treating an ear recited in claim 20 wherein said step of moving comprises moving the treatment member against the stapes to displace the stapes footplate.

23. The method for treating an ear recited in claim 20 wherein said step of disposing comprises contacting the selected portion of the partition with the treatment member.

24. The method for treating an ear recited in claim 20 wherein said step of moving comprises reciprocating the treatment member.

25. The method for treating an ear recited in claim 20 wherein said step of moving comprises vibrating the treatment member.

26. The method for treating an ear recited in claim 20 wherein said step of moving comprises oscillating the treatment member.

27. A method for treating an ear having a middle ear and an inner ear separated by a partition comprising the steps of
    disposing a treatment device within the middle ear adjacent the partition; and
    moving at least a portion of the treatment device at an infrasonic frequency to displace the partition to influence fluid in the inner ear.

28. The method for treating an ear recited in claim 27 where said step of moving includes stimulating motion of fluid in the inner ear.

29. The method for treating an ear recited in claim 27 wherein said step of moving comprises alleviating the symptoms of Meniere's disease.

30. The method for treating an ear recited in claim 27 wherein said step of moving comprises alleviating vertigo.

31. The method for treating an ear recited in claim 27 wherein said step of moving comprises alleviating tinnitus.

32. The method for treating an ear recited in claim 27 wherein said step of moving comprises alleviating fullness of the ear.

33. The method for treating an ear recited in claim 27 wherein said step of moving comprises alleviating hearing loss.

34. The method for treating an ear recited in claim 27 wherein said step of disposing comprises disposing a treatment member of the treatment device in contact with the partition and said step of moving comprises supplying a signal to the treatment member and causing the treatment member to move in accordance with the signal.

35. The method for treating an ear recited in claim 27 wherein said step of disposing includes implanting at least the portion of the treatment device in the middle ear.

36. The method for treating an ear recited in claim 35 wherein said step of implanting includes implanting a treatment member of the treatment device in the middle ear and said step of moving includes driving the treatment member to displace the partition from externally of the ear.

37. The method for treating an ear recited in claim 35 wherein said step of implanting includes implanting a treatment member of the treatment device in the middle ear and implanting a driver of the treatment device in the ear, and said step of moving includes driving the treatment member to displace the partition via the driver.

* * * * *